(12) United States Patent
Kasemi et al.

(10) Patent No.: US 9,796,661 B2
(45) Date of Patent: Oct. 24, 2017

(54) AMINE FOR LOW-EMISSION EPOXY RESIN PRODUCTS

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/106,921

(22) PCT Filed: Jan. 26, 2015

(86) PCT No.: PCT/EP2015/051434
§ 371 (c)(1),
(2) Date: Jun. 21, 2016

(87) PCT Pub. No.: WO2015/117846
PCT Pub. Date: Aug. 13, 2015

(65) Prior Publication Data
US 2017/0029364 A1    Feb. 2, 2017

(30) Foreign Application Priority Data
Feb. 7, 2014    (EP) .................................... 14154363

(51) Int. Cl.
| | | |
|---|---|---|
| *C07C 217/30* | (2006.01) | |
| *C08G 59/50* | (2006.01) | |
| *C09D 163/10* | (2006.01) | |
| *C07C 213/08* | (2006.01) | |
| *C08G 59/64* | (2006.01) | |
| *C09D 163/00* | (2006.01) | |

(52) U.S. Cl.
CPC ......... *C07C 217/30* (2013.01); *C07C 213/08* (2013.01); *C08G 59/5013* (2013.01); *C08G 59/64* (2013.01); *C09D 163/00* (2013.01); *C09D 163/10* (2013.01)

(58) Field of Classification Search
CPC ...................................................... C08G 59/64
See application file for complete search history.

(56) References Cited

FOREIGN PATENT DOCUMENTS

| | | |
|---|---|---|
| CN | 101775196 A | 7/2010 |
| CN | 103030931 A | 4/2013 |
| CN | 104193985 A | 12/2014 |
| GB | 1258454 A | 12/1971 |
| WO | 2007/060091 A1 | 5/2007 |

OTHER PUBLICATIONS

Apr. 20, 2015 International Search Report issued in International Patent Application No. PCT/EP2015/051434.
Aug. 24, 2017 Office Action issued in Chinese Patent Application No. 201580005977.5.

*Primary Examiner* — Kuo-Liang Peng
(74) *Attorney, Agent, or Firm* — Oliff PLC

(57) ABSTRACT

The present invention relates to an amine of the formula (I) which is an adduct of 1,2-propylenediamine with an aryl monoglycidyl ether, to the use thereof as part of a hardener for epoxy resins, and to epoxy resin compositions obtained therewith. The amine of the formula (I) is preparable in a simple process in high purity, is of very low viscosity and is especially suitable for the curing of epoxy resins. It allows low-emission epoxy resin compositions which have good workability and which cure even under cold and damp conditions, quickly and without blushing effects, to form very hard products of high surface quality that display virtually no yellowing on exposure to light.

16 Claims, No Drawings

AMINE FOR LOW-EMISSION EPOXY RESIN PRODUCTS

TECHNICAL FIELD

The invention pertains to the field of amines, of hardeners for epoxy resins, of epoxy resin products, and of use thereof, particularly as coatings, coverings, and paints.

PRIOR ART

Epoxy resin products that are suitable for coatings use are to have a very low viscosity, allowing them to be readily workable and self-leveling at ambient temperature. Furthermore, they are to cure very quickly and without interference, even under damp and cold conditions, and to form an even surface without haze, spots or craters. Lastly, a cured coating is to possess high hardness but low brittleness, in order to withstand mechanical stress as effectively as possible. For visually demanding applications, an example being floor coverings, moreover, a coating is to exhibit high gloss and as little as possible propensity to suffer yellowing under the effect of light.

Hardeners known from the prior art for epoxy resin coatings typically comprise adducts of polyamines with diepoxides, particularly with liquid bisphenol resins. Such adducts do allow rapid curing, but have a very high viscosity, and so diluents are typically used in the hardeners. The diluents enhance the workability, reduce the brittleness of the coating, and improve the surface quality, by reducing the incidence of blushing effects. "Blushing effects" is a term used to refer to surface deficiencies which occur in the course of curing, such as hazing, spotting, roughness, and stickiness, and which are caused by salt formation (blushing) of amines with atmospheric carbon dioxide ($CO_2$) and occur particularly when humidity is high and temperatures are low. The diluents commonly employed, especially benzyl alcohol and also glycols and alkylphenols, are inert toward epoxy resins at room temperature and are therefore not incorporated into the resin matrix in the course of curing.

Nowadays, however, the desire is increasingly for low-emission products, which after curing have a low level of substances that may be given off by processes of evaporation or diffusion. For low-emission epoxy resin products, therefore, diluents which cannot be incorporated can be used only in very small amounts, or not at all.

Another means of diluting the hardener component is to use increased amounts of small amines in the hardener component. Such amines, however, such as dimethylaminopropylamine or diethylenetriamine, for example, have a strong odor, are very irritant to skin and eyes, have a sensitizing effect, and result in increased incidence of blushing effects.

Moreover, amine adducts of monoepoxides, especially monoglycidyl ethers, can be used that have a significantly reduced viscosity relative to amine adducts of diepoxides, and that therefore can be used with less diluents. One low-viscosity adduct known is obtained from the aliphatic amine 1,5-diamino-2-methylpentane (MPMD) and cresyl glycidyl ether. This opens access to epoxy resin coatings with a low-diluent or diluent-free formulation, which cure largely without blushing effects. Nevertheless, there is still room for improvement in the cure rate and development of strength, in the ultimate hardness, and in the viscosity of such coatings.

SUMMARY OF THE INVENTION

It is an object of the present invention, therefore, to provide a low-viscosity and low-odor amine that allows the formulation of low-emission epoxy resins which cure rapidly, even at relatively low temperatures, to form high-quality films or structures of high surface quality and strength and which suffer virtually no yellowing under the effect of light.

Surprisingly it has been found that an amine of the formula (I) achieves this object very well. It has a low melting point, is of surprisingly low viscosity and low odor, and can be prepared in high purity in a simple process from substances which are inexpensive and readily available commercially.

When used as a hardener, the amine of the formula (I) opens access to epoxy resin products of low viscosity and hence ready workability, featuring rapid development of strength and high surface quality, even at low temperatures.

Both under standard conditions and under damp and cold conditions, such as at 8° C. and 80% relative humidity, for example, areal application produces clear films of high gloss which suffer virtually no yellowing under the effect of light and which are free from spotting, unevenness, structures, or marks. The amine of the formula (I) has a sterically hindered primary amino group and a secondary amino group which is activated by the adjacent hydroxyl group, and is compatible with commercial liquid epoxy resins based on bisphenol A and/or F. In comparison to the use of similar adducts of, for example, DETA, MPMD, TMD, 1,3-BAC or IPDA, the amine of the formula (I) can be used to obtain epoxy resin products having a lower viscosity and/or a better surface quality. The amine of the formula (I) allows access to epoxy resin compositions which are of low viscosity even without diluent and without small, intensely odorous amines, and which cure, even at low temperatures and on early exposure to water splashing, to form defect-free, high-quality films of high gloss which suffer virtually no yellowing under the effect of light.

Further aspects of the invention are the subjects of further independent claims. Particularly preferred embodiments of the invention are subjects of the dependent claims.

CERTAIN EMBODIMENTS OF THE INVENTION

The invention provides an amine of the formula (I),

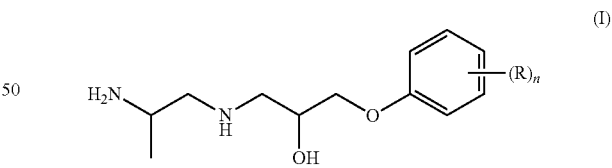

where
R is an alkyl, cycloalkyl, aralkyl or alkoxy radical having 1 to 22 carbon atoms, which optionally comprises unsaturated fractions; and
n is 0 or 1 or 2 or 3.

Substance names beginning with "poly" such as polyamine, polyol or polyepoxide identify substances which formally per molecule contain two or more of the functional groups which appear in their name.

A "primary amino group" is an $NH_2$ group which is bonded to an organic radical, and a "secondary amino group" is an NH group which is bonded to two organic radicals, which may also together be part of a ring.

"Amine hydrogen" refers to the hydrogen atoms of primary and secondary amino groups.

"Amine hydrogen equivalent weight" refers to the weight fraction of a hardener or of an amine per amine hydrogen present in the hardener or in the amine.

An "unincorporable diluent" is a substance which is soluble in and lowers the viscosity of an epoxy resin and which is not incorporated covalently into the resin matrix when the epoxy resin is cured.

The term "viscosity" refers in the present document to the dynamic viscosity or shear viscosity, defined by the ratio between the shear stress and the shear rate (rate gradient) and determined as described in DIN EN ISO 3219.

The radicals R in the formula (I) may be identical to or different from one another if n is 2 or 3.

Preferably n is 0 or 1 or 2, more particularly 1. An amine of the formula (I) of this kind has a particularly low viscosity.

Preferably R is an alkyl or alkoxy radical having 1 to 18 carbon atoms, which optionally comprises unsaturated fractions, and more preferably is methyl, tert-butyl, unsaturated fatty alkyl having 12 to 18, more particularly 15, C atoms, or methoxy.

More particularly R is methyl, preferably 2-methyl.

Most preferably n is 1 and R is methyl, more particularly 2-methyl.

These amines of the formula (I) are particularly readily obtainable and are notable for particularly low viscosity and particularly good properties as a constituent of epoxy resin products, more particularly for rapid curing and a high ultimate hardness.

With further preference, n is 1 and R is tert-butyl, more particularly 4-tert-butyl. These amines of the formula (I) allow especially attractive surfaces.

With further preference, n is 1 and R is fatty alkyl having 15 C atoms and unsaturated fractions, especially in 3-position. These amines of the formula (I) are of particularly low viscosity and produce epoxy resin products with relatively soft properties.

The amine of the formula (I) is preferably obtainable from the reaction of 1,2-propylenediamine with an aryl monoglycidyl ether. It may also be referred to as an adduct of 1,2-propylenediamine with the aryl monoglycidyl ether.

Preferred aryl monoglycidyl ethers are the glycidyl ethers of phenol, cresol, guajacol, 4-methoxyphenol, tert-butylphenol or cardanol. This cardanol is a distillate from cashew nut shell oil, containing 8,11,14-pentadecatrienylphenol as its principal constituent.

Particularly preferred aryl monoglycidyl ethers are all isomeric cresyl glycidyl ethers and any desired mixtures thereof, especially 2-cresyl glycidyl ether. Preference is given to using a commercially available cresyl glycidyl ether, more particularly Araldite® DY-K (from Huntsman), Polypox™ R6 (from Dow), Heloxy™ KR (from Momentive), or Erisys® GE-10 (from CVC Spec. Chem.).

In a preferred preparation process, 1,2-propylenediamine is reacted with an aryl glycidyl ether in such a way that there is at least one mole of 1,2-propylenediamine present per mole of aryl glycidyl ether.

In a particularly preferred preparation process there is more than one mole of 1,2-propylenediamine present per mole of aryl glycidyl ether, and unreacted 1,2-propylenediamine is distilled off after the reaction, preferably by thin-film or, in particular, thin-layer distillation.

Preference is given to a preparation process with a 1,2-propylenediamine/aryl glycidyl ether molar ratio in the range from 1.1 to 5, more preferably 1.5 to 4, and subsequent distillative removal of unreacted 1,2-propylenediamine.

An amine of the formula (I) thus prepared is notable for particularly high purity and particularly low viscosity, and produces epoxy resin products having particularly good workability and particularly attractive surfaces.

The reaction is carried out preferably by slow metered addition of aryl monoglycidyl ether to an initial charge of 1,2-propylenediamine, the temperature of the reactants being maintained preferably in the range from 40 to 120° C., more particularly 50 to 110° C.

The reaction product from this preparation may comprise, as well as the amine of the formula (I), fractions of further amine adducts, particularly of the amine of the formula (II) and/or of the amine of the formula (III). Owing to the difference in reactivity between the two amino groups of 1,2-propylenediamine, and to the excess of 1,2-propylenediamine over the aryl monoglycidyl ether that is used with preference in the reaction, the distillative removal of the excess 1,2-propylenediamine, however, typically produces very pure amine of the formula (I).

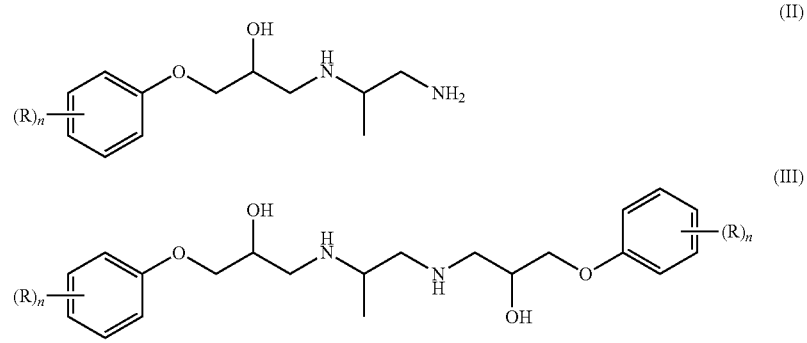

In the formulae (II) and (III), R and n have the definitions already stated.

The amine of formula (I) has very advantageous properties. It is of low viscosity and has only a slight amine odor. Its melting point is low enough that even at winter temperatures it can be handled and transported in the liquid state without any risk of crystallizing. It possesses a sterically hindered primary amino group and a beta-hydroxy-substituted secondary amino group. This makes it particularly suitable as a hardener for epoxy resins, where it produces low-viscosity compositions having very attractive surfaces, which cure rapidly, even under damp and cold conditions, and without blushing-related defects, to a high ultimate hardness.

The invention further provides for the use of at least one amine of the formula (I) in a hardener for epoxy resins.

The amine of the formula (I) here has the advantage that it is of low volatility, low odor and sufficiently low viscosity to allow readily workable epoxy resin products even without the use of solvents or diluents. With an amine of the formula (I), low-viscosity epoxy resin compositions having very attractive and cold conditions, and without blushing-related defects, and which suffer virtually no yellowing under the effect of light.

The amine of the formula (I) can be used alone or together with other amines and/or accelerators and optionally further substances as hardener for epoxy resins.

The hardener preferably comprises the amine of the formula (I) in an amount such that 5 to 100%, preferably 10 to 90%, more preferably 15 to 80%, more particularly 15 to 70%, of the amine hydrogens in the hardener that are reactive toward epoxide groups originate from the amine of the formula (I). A hardener of this kind offers a good balance between low viscosity and rapid curing and enables epoxy resin products having attractive surfaces and high strengths.

As well as the amine of the formula (I), the hardener preferably comprises at least one further polyamine having at least two amine hydrogens that are active toward epoxide groups.

Suitable for this purpose in particular are the following polyamines:

aliphatic, cycloaliphatic or arylaliphatic primary diamines, especially 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11 neodiamine), 1,6-hexanediamine, 2,5-dimethyl-1,6-hexanediamine, 2,2,4- and 2,4,4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3-, and 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane, 1-amino-3-aminomethyl-3,5,5-trimethylcyclohexane (=isophoronediamine or IPDA), 2- and 4-methyl-1,3-diaminocyclohexane and mixtures thereof, 1,3-bis(aminomethyl)cyclohexane (1,3-BAC), 1,4-bis(aminomethyl)cyclohexane, 2,5(2,6)-bis(aminomethyl)-bicyclo[2.2.1]heptane (NBDA), 3(4),8(9)-bis(aminomethyl)tricyclo-[5.2.1.0$^{2,6}$]decane (TCD diamine), 1,4-diamino-2,2,6-trimethylcyclohexane (TMCDA), 1,8-menthanediamine, 3,9-bis(3-aminopropyl)-2,4,8,10-tetraoxa-spiro[5.5]undecane or 1,3-bis(aminomethyl)benzene (MXDA);

polyamines containing tertiary amino groups and having two or three primary aliphatic amino groups, especially N,N'-bis(aminopropyl)piperazine, N,N-bis(3-aminopropyl)methylamine, N,N-bis(3-aminopropyl)ethylamine, N,N-bis(3-aminopropyl)propylamine, N,N-bis(3-aminopropyl)cyclohexylamine, N,N-bis(3-aminopropyl)-2-ethylhexylamine, tris(2-aminoethyl)amine, tris(2-aminopropyl)amine, tris(3-aminopropyl)amine, or the products from the double cyano ethylation and subsequent reduction of fatty amines derived from natural fatty acids, such as N,N-bis(3-aminopropyl)dodecylamine or N,N-bis(3-aminopropyl)tallowalkylamine, available as Triameen® Y12D or Triameen® YT (from Akzo Nobel);

aliphatic primary polyamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine and higher oligomers of these diamines, bis(3-aminopropyl)polytetrahydrofurans and other polytetrahydrofurandiamines, cycloaliphatic diamines containing ether groups, from the propoxylation and subsequent amination of 1,4-dimethylolcyclohexane, available especially as Jeffamine® RFD-270 (from Huntsman), or polyoxyalkylenedi- or -triamines, which are typically products of the amination of polyoxyalkylenedi- and -triols and are available, for example, under the name Jeffamine® (from Huntsman), under the name Polyetheramine (from BASF) or under the name PC Amine® (from Nitroil), especially Jeffamine® D-230, Jeffamine® D-400, Jeffamine® D-2000, Jeffamine® D-4000, Jeffamine® T-403, Jeffamine® T-3000, Jeffamine® T-5000, Jeffamine® EDR-104, Jeffamine® EDR-148 and Jeffamine® EDR-176, and also corresponding amines from BASF or Nitroil;

primary diamines having secondary amino groups, such as especially 3-(2-aminoethypaminopropylamine, bis(hexamethylene)triamine (BHMT), diethylenetriamine (DETA), triethylenetetramine (TETA), tetraethylenepentamine (TEPA), pentaethylenehexamine (PEHA), and higher homologs of linear polyethyleneamines such as polyethylenepolyamine having 5 to 7 ethyleneamine units (so-called "higher ethylenepolyamine", HEPA), products from the multiple cyanoethylation or cyanobutylation and subsequent hydrogenation of primary diamines and polyamines having at least two primary amino groups, such as dipropylenetriamine (DPTA), N-(2-aminoethyl)-1,3-propanediamine (N3 amine), N,N'-bis(3-aminopropyl)-ethylenediamine (N4 amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N,N'-bis(3-amino-1-ethylpropyl)-2-methyl-1,5-pentanediamine;

polyamines having one primary and at least one secondary amino group, such as especially N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, N-(2-aminoethyl)piperazine, N-methyl-1,3-propanediamine, N-butyl-1,3-propanediamine, N-(2-ethylhexyl)-1,3-propanediamine, N-cyclohexyl-1,3-propanediamine, 3-methylamino-1-pentylamine, 3-ethylamino-1-pentylamine, 3-cyclohexylamino-1-pentylamine, fatty diamines such as N-cocoalkyl-1,3-propanediamine, products from the Michael-like addition reaction of primary aliphatic diamines with acrylonitrile, maleic or fumaric diesters, citraconic diesters, acrylic and methacrylic esters, acrylamides and methacrylamides, and itaconic diesters, reacted in a 1:1 molar ratio, and additionally products from the partial reductive alkylation of primary polyamines with aldehydes or ketones, especially products of N-monoalkylation of the aforementioned polyamines having two primary amino groups, especially of 1,6-hexanediamine, MPMD, 1,3-BAC, 1,4-bis(amino-methyl)cyclohexane, MXDA, BHMT, DETA, TETA, TEPA, DPTA, N3 amine or N4 amine, the alkyl group being preferably benzyl, isobutyl, hexyl, and 2-ethylhexyl, and also, furthermore, partly styrenized polyamines, particularly the commercially available Gaskamine® 240 (from Mitsubishi Gas Chemical);

secondary diamines, such as especially products of N,N'-dialkylation of the aforementioned polyamines having two primary amino groups, especially N,N'-dialkylation products of 1,6-hexanediamine, MPMD, 1,3-BAC, 1,4-bis(aminomethyl)cyclohexane, MXDA, BHMT, DETA, TETA, TEPA, DPTA, N3 amine or N4 amine, preferred alkyl groups being 2-phenylethyl, benzyl, isobutyl, hexyl or 2-ethylhexyl.

As polyamine having at least two amine hydrogens that are active toward epoxide groups, preference is given to primary diamines and/or polyamines having at least one secondary amino group.

A hardener with at least one primary diamine permits epoxy resin products with a particularly low viscosity and/or a particularly rapid development of strength. In one preferred embodiment the hardener as well as the amine of the formula (I) comprises at least one primary diamine selected from the group consisting of 2,2,4- and 2,4,4-trimethylhexamethylenediamine (TMD), 1-amino-3-aminomethyl-3,5,5-trimethylcyclohexane (IPDA), 1,3-bis(aminomethyl)benzene (MXDA), 1,3-bis(aminomethyl)cyclohexane (1,3-BAC), 1,4-bis(aminomethyl)cyclohexane, bis(4-aminocyclohexyl)methane, bis(4-amino-3-methylcyclohexyl)methane, 2,5(2,6)-bis(aminomethyl)bicyclo[2.2.1]heptane (NBDA), 3(4),8(9)-bis(aminomethyl)tricyclo[5.2.1.0$^{2,6}$]decane (TCD diamine), and polyamines containing ether groups and having an average molecular weight of up to 500 g/mol.

These polyamines are available commercially and produce hardeners which are free from particularly volatile amines.

Particularly preferred among these are the polyamines containing ether groups, especially polyoxypropylenediamines such as, in particular, Jeffamine® D-230 (from Huntsman) or corresponding amines from BASF or Nitroil, and also cycloaliphatic diamines containing ether groups, from the propoxylation and subsequent amination of 1,4-dimethylolcyclohexane, especially Jeffamine® RFD-270 (from Huntsman). The polyamines containing ether groups produce epoxy resin coatings having particularly low viscosity, rapid curing, and high impact strength.

Also particularly preferred among these is IPDA. This cycloaliphatic amine produces epoxy resin products having very attractive surfaces, which are particularly stable toward weathering and chemicals.

Also particularly preferred among these is 1,3-BAC. This cycloaliphatic amine produces epoxy resin products having a particularly rapid development of strength and high stability toward weathering and chemicals.

Also particularly preferred among these is MXDA. This arylaliphatic amine produces epoxy resin products having particularly rapid development of strength and particularly attractive surfaces.

A hardener which as well as the amine of the formula (I) comprises at least one further polyamine having at least one secondary amino group produces epoxy resin products having especially low viscosity and particularly high impact strength.

Preferred as polyamine having at least one secondary amino group are N-monoalkylated and N,N'-dialkylated primary polyamines and mixtures thereof, as obtained in particular by reductive alkylation of primary polyamines with aldehydes or ketones and hydrogen. Aldehydes are preferred over ketones in this respect. Preferred polyamines are those in which 50 to 100%, preferably 50 to 80%, especially 50 to 65%, of the originally primary amino groups are present in the form of secondary amino groups.

Further preferred polyamines having at least one secondary amino group are products of the partial styrenization of primary diamines, especially Gaskamine® 240 (from Mitsubishi Gas Chemical).

In one preferred embodiment the hardener as well as the amine of the formula (I) comprises at least one polyamine having at least one secondary amino group, selected from the group consisting of N-monoalkylated 1,6-hexanediamine, N,N'-dialkylated 1,6-hexanediamine, N-monoalkylated 1,5-diamino-2-methylpentane, N,N'-dialkylated 1,5-diamino-2-methylpentane, N-monoalkylated 1,3-bis(aminomethyl)cyclohexane, N,N'-dialkylated 1,3-bis(aminomethyl)cyclohexane, N-monoalkylated 1,4-bis(amino-methyl)cyclohexane, N,N'-dialkylated 1,4-bis(aminomethyl)cyclohexane, N-monoalkylated 1,3-bis(aminomethyl)benzene, N,N'-dialkylated 1,3-bis(aminomethyl)benzene, N-monoalkylated BHMT, N,N'-dialkylated BHMT, N-monoalkylated DETA, N,N'-dialkylated DETA, N-monoalkylated TETA, N,N'-dialkylated TETA, N-monoalkylated TEPA, N,N'-dialkylated TEPA, N-monoalkylated DPTA, N,N'-dialkylated DPTA, N-monoalkylated N3-amine, N,N'-dialkylated N3-amine, N-monoalkylated N4-amine and N,N'-dialkylated N4-amine, the alkyl groups being selected in each case from the group consisting of benzyl, 2-phenylethyl, isobutyl, hexyl, and 2-ethylhexyl. Possible here are any desired combinations between the stated amines and the stated alkyl groups.

These polyamines produce epoxy resin products with particularly low viscosity, high surface quality, and particularly high impact strength.

Preferred among these are mono- and/or dibenzylated 1,3-bis(aminomethyl)-benzene, mono- and/or di-2-ethylhexylated 1,3-bis(aminomethyl)benzene, and partially styrenized 1,3-bis(aminomethyl)benzene, such as especially Gaskamine® 240 (from Mitsubishi Gas Chemical). These arylaliphatic polyamines are especially compatible with commercial epoxy resins and produce epoxy resin products featuring rapid development of strength and very high surface quality.

It can be advantageous if in the hardener as well the amine of the formula (I) there are both at least one primary diamine and at least one polyamine having at least one secondary amino group. Hardeners of this kind produce epoxy resin products having particularly low viscosity, rapid development of strength, high hardness, and high impact strength. Particularly preferred are combinations of polyamines containing ether groups with N-monoalkylated and/or N,N'-dialkylated primary diamines.

One especially preferred hardener, as well as the amine of the formula (I), comprises at least one diamine containing ether groups and optionally a further primary diamine. Preferred as diamine containing ether groups are Jeffamine® D-230 from Huntsman or a corresponding amine from BASF or Nitroil, and Jeffamine RFD-270 from Huntsman, more particularly Jeffamine® D-230 from Huntsman or a corresponding amine from BASF or Nitroil.

In this case preferably
10 to 90%, more preferably 15 to 80%, especially 15 to 70% of the amine hydrogens in the hardener that are reactive toward epoxide groups originate from the amine of the formula (I), and
10 to 60%, preferably 10 to 50%, especially 20 to 50%, of the amine hydrogens in the hardener that are reactive toward epoxide groups originate from the diamine containing ether groups.

A hardener of this kind preferably comprises amine of the formula (I) at at least 5 weight %, preferably at least 10 weight %, more particularly at least 20 weight %.

A hardener of this kind preferably comprises amine of the formula (I) at less than 90 weight %, preferably less than 85 weight %, more particularly less than 80 weight %.

Another especially preferred hardener, as well as the amine of the formula (I), comprises at least one diamine containing ether groups and at least one polyamine having at least one secondary amino group.

In this case preferably
15 to 80, especially 15 to 70% of the amine hydrogens in the hardener that are reactive toward epoxide groups originate from the amine of the formula (I),
15 to 60% of the amine hydrogens in the hardener that are reactive toward epoxide groups originate from the diamine containing ether groups, and
10 to 35%, preferably 10 to 20%, of the amine hydrogens in the hardener that are reactive toward epoxide groups originate from the polyamine having at least one secondary amino group.

The hardener preferably further comprises at least one accelerator. Suitable accelerators are substances which accelerate the reaction between amino groups and epoxide groups, especially acids or compounds which can be hydrolyzed to acids, particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecyl-benzenesulfonic acid, sulfonic esters, other organic or inorganic acids such as, in particular, phosphoric acid, or mixtures of the aforementioned acids and acid esters; additionally, tertiary amines such as, in particular, 1,4-diazabicyclo[2.2.2]octane, benzyldimethylamine, α-methylbenzyldimethyl-amine, triethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular, benzyltrimethylammonium chloride, amidines such as, in particular, 1,8-diazabicyclo[5.4.0]undec-7-ene, guanidines such as, in particular, 1,1,3,3-tetramethylguanidine, phenols, especially bisphenols, phenolic resins, and Mannich bases such as, in particular, 2-(dimethylaminomethyl)phenol, 2,4,6-tris(dimethylaminomethyl)phenol and polymers of phenol, formaldehyde, and N,N-dimethyl-1,3-propanediamine, phosphites such as, in particular, di- and triphenyl phosphites, and also compounds containing mercapto groups. Preferred accelerators are acids, tertiary amines or Mannich bases. Particularly preferred are salicylic acid and/or 2,4,6-tris(dimethylaminomethyl)phenol.

The hardener preferably comprises no high-volatility amines. The hardener is preferably free from 1,2-propylenediamine or contains only traces thereof, more particularly less than 0.1 weight %. With further preference the hardener is free from dimethylaminopropylamine and from other amines with comparably high volatility.

In one preferred embodiment the hardener is largely free from amines having a molecular weight of below 120 g/mol, more particularly below 150 g/mol, very preferably below 180 g/mol. The hardener preferably contains less than 2 weight %, more particularly less than 1 weight %, of amines having a molecular weight of below 120 g/mol, more particularly below 150 g/mol, very preferably below 180 g/mol. A hardener of this kind is particularly advantageous from a toxicological standpoint and produces particularly attractive surfaces when areally applied.

The hardener may further comprise at least one unincorporable diluent. Particularly suitable unincorporable diluents are xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as, for example, Solvesso® products (from Exxon), alkylphenols such as tert-butylphenol, nonylphenol, dodecylphenol, and 8,11,14-pentadecatrienylphenol (Cardanol, from cashew shell oil, available for example as Cardolite NC-700 from Cardolite Corp., USA), styrenized phenol, bisphenols, aromatic hydrocarbon resins, especially grades containing phenol groups, alkoxylated phenol, especially ethoxylated or propoxylated phenol, more particularly 2-phenoxyethanol, adipates, sebacates, phthalates, benzoates, organic phosphoric or sulfonic esters or sulfonamides. Preferred unincorporable diluents are benzyl alcohol, dodecylphenol, tert-butylphenol, styrenized phenol, ethoxylated phenol, or aromatic hydrocarbon resins containing phenol groups, more particularly the Novares® products LS 500, LX 200, LA 300, and LA 700 (from Rutgers).

The hardener preferably does not contain, or contains only at a low level, any unincorporable diluents, more preferably less than 25 weight %, more particularly less than 10 weight %, and most preferably less than 5 weight %. In particular no unincorporable diluents are added to the hardener.

The hardener may further comprise aromatic polyamines, more particularly m- and p-phenylenediamine, 4,4'-, 2,4'-, and 2,2'-diaminodiphenylmethane, 3,3'-dichloro-4,4'-diaminodiphenylmethane (MOCA), 2,4- and 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzene-sulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl 4-chloro-3,5-diaminobenzoate.

The hardener may further comprise additional adducts, more particularly adducts of 1,2-propylenediamine with aliphatic monoepoxides or with diepoxides, or adducts of other primary diamines with mono- or diepoxides, and also reaction products of amines and epichlorohydrin, particularly that of 1,3-bis(aminomethyl)benzene, available commercially as Gaskamine® 328 (from Mitsubishi Gas Chemical).

The hardener may further comprise polyamidoamines, which constitute reaction products of a mono- or polybasic carboxylic acid, and/or the esters or anhydrides thereof, particularly of a dimer fatty acid, with an aliphatic, cycloaliphatic or aromatic polyamine which is used in a stoichiometric excess, more particularly a polyalkyleneamine such as, for example, DETA or TETA, more particularly the commercially available polyamidoamines Versamid® 100, 125, 140, and 150 (from Cognis), Aradur® 223, 250, and 848 (from Huntsman), Euretek® 3607 and 530 (from Huntsman), and Beckopox® EH 651, EH 654, EH 655, EH 661, and EH 663 (from Cytec).

The hardener may further comprise Mannich bases, which represent reaction products of a Mannich reaction between phenols and aldehydes, especially formaldehyde, and with polyamines. Particularly suitable are the Mannich bases of cardanol that are also referred to as phenalkamines, examples being the commercially available Phenalkamines Cardolite® NC-541, NC-557, NC-558, NC-566, Lite 2001, and Lite 2002 (from Cardolite), Aradur® 3440, 3441, 3442, and 3460 (from Huntsman), and Beckopox® EH 614, EH 621, EH 624, EH 628, and EH 629 (from Cytec).

The hardener may further comprise monoamines such as hexylamine and benzylamine.

The hardener may further comprise compounds containing mercapto groups, more particularly the following:
  liquid mercaptan-terminated polysulfide polymers, known under the brand name Thiokol® (from Morton Thiokol; available for example from SPI Supplies, or from Toray Fine Chemicals), especially the grades LP-3, LP-33, LP-980, LP-23, LP-55, LP-56, LP-12, LP-31, LP-32, and LP-2, and additionally known under the brand name Thioplast® (from Akzo Nobel), especially the grades G 10, G 112, G 131, G 1, G 12, G 21, G 22, G 44, and G 4;
  mercaptan-terminated polyoxyalkylene ethers, obtainable for example by reaction of polyoxyalkylenediols and -triols either with epichlorohydrin or with an alkylene oxide, followed by sodium hydrogen sulfide;
  mercaptan-terminated compounds in the form of polyoxyalkylene derivatives, known under the brand name Capcure® (from Cognis), especially the grades WR-8, LOF, and 3-800;
  polyesters of thiocarboxylic acids, examples being pentaerythritol tetramercaptoacetate, trimethylolpropane trimercaptoacetate, glycol dimercaptoacetate, pentaerythritol tetra(3-mercaptopropionate), trimethylolpropane tri(3-mercaptopropionate), and glycol di(3-mercaptopropionate), and also the esterification products of polyoxyalkylenediols and -triols, ethoxylated trimethylolpropane, and polyester diols with thiocarboxylic acids such as thioglycolic acid and 2- or 3-mercaptopropionic acid; and
  other compounds containing mercapto groups, such as especially 2,4,6-trimercapto-1,3,5-triazine, 2,2'-(ethylenedioxy)diethanethiol (triethylene glycol dimercaptan), and ethanedithiol.

The invention further provides an epoxy resin composition comprising at least one epoxy resin and the hardener described above.

Suitable epoxy resin comprises customary technical epoxy resins. These resins are obtained in a conventional way, as for example from the oxidation of the corresponding olefins or from the reaction of epichlorohydrin with the corresponding polyols, polyphenols, or amines.

Particularly suitable as epoxy resin are what are called liquid polyepoxy resins, identified below as "liquid resin". These have a glass transition temperature of below 25° C.

Likewise possible as epoxy resin are what are called solid resins, which have a glass transition temperature above 25° C. and can be comminuted into powders which are pourable at 25° C.

Suitable epoxy resins are, in particular, aromatic epoxy resins, more particularly the glycidylization products of:
  bisphenol A, bisphenol F or bisphenol A/F, where A stands for acetone and F for formaldehyde, which have served as reactants in the preparation of these bisphenols. In the case of bisphenol F, there may also be positional isomers present, derived in particular from 2,4'- and 2,2'-hydroxyphenylmethane;
  dihydroxybenzene derivatives such as resorcinol, hydroquinone or pyrocatechol;
  further bisphenols or polyphenols such as bis(4-hydroxy-3-methyl-phenyl)methane, 2,2-bis(4-hydroxy-3-methylphenyl)propane (bisphenol C), bis(3,5-dimethyl-4-hydroxyphenyl)methane, 2,2-bis(3,5-dimethyl-4-hydroxyphenyl)propane, 2,2-bis(3,5-dibromo-4-hydroxyphenyl)propane, 2,2-bis(4-hydroxy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), 4,4'-dihydroxybenzophenone, bis(2-hydroxynaphth-1-yl)methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;
  condensation products of phenols with formaldehyde which are obtained under acidic conditions, such as phenol novolaks or cresol novolaks, also called bisphenol F novolaks;
  aromatic amines, such as aniline, toluidine, 4-aminophenol, 4,4'-methylene-diphenyldiamine, 4,4'-methylene-diphenyldi(N-methyl)amine, 4,4'-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, especially
  glycidyl ethers of saturated or unsaturated, branched or unbranched, cyclic or open-chain di-, tri- or tetra-functional $C_2$ to $C_{30}$ alcohols, especially ethylene glycol, propylene glycol, butylene glycol, hexanediol, octanediol, polypropylene glycols, dimethylolcyclohexane, neopentyl glycol, dibromo-neopentyl glycol, castor oil, trimethylolpropane, trimethylolethane, pentaerythritol, sorbitol or glycerol, and also alkoxylated glycerol or alkoxylated trimethylolpropane;

a hydrogenated liquid bisphenol A, F or A/F resin, or the glycidylization products of hydrogenated bisphenol A, F or A/F;

an N-glycidyl derivative of amides or heterocyclic nitrogen bases, such as triglycidyl cyanurate or triglycidyl isocyanurate, and also reaction products of epichlorohydrin and hydantoin;

epoxy resins from the oxidation of olefins, such as especially vinylcyclo-hexene, dicyclopentadiene, cyclohexadiene, cyclododecadiene, cyclododecatriene, isoprene, 1,5-hexadiene, butadiene, polybutadiene or divinylbenzene.

The epoxy resin is preferably a liquid resin based on a bisphenol, more particularly a diglycidyl ether of bisphenol A, bisphenol F or bisphenol A/F, as are available commercially, for example from Dow, Huntsman, and Momentive. These liquid resins have a viscosity which is low for epoxy resins and in the cured state they have good properties as coatings. They may be present optionally in combination with solid bisphenol A resin or bisphenol F novolak epoxy resin.

The epoxy resin may comprise a reactive diluent, more particularly a reactive diluent containing at least one epoxide group. Examples of suitable reactive diluents are the glycidyl ethers of mono- or polyhydric phenols or aliphatic or cycloaliphatic alcohols, such as especially the polyglycidyl ethers of diols or polyols, as already mentioned, and also, furthermore, in particular, phenyl glycidyl ether, cresyl glycidyl ether, benzyl glycidyl ether, p-n-butylphenyl glycidyl ether, p-tert-butylphenyl glycidyl ether, nonylphenyl glycidyl ether, allyl glycidyl ether, butyl glycidyl ether, hexyl glycidyl ether, 2-ethylhexyl glycidyl ether, and also glycidyl ethers of natural alcohols, such as $C_8$ to $C_{10}$ alkyl glycidyl ethers or $C_{12}$ to $C_{14}$ alkyl glycidyl ethers, for example. Adding a reactive diluent to the epoxy resin brings about a reduction in the viscosity, and also a reduction in the glass transition temperature and the mechanical values.

The epoxy resin composition optionally comprises further constituents, especially auxiliaries and additives that are customarily used in epoxy resin compositions, examples being the following:

solvents, diluents, film-forming assistants or extenders, such as in particular the unincorporable diluents already stated;

reactive diluents, particularly reactive diluents containing epoxide groups, as mentioned above, or epoxidized soybean oil or linseed oil, compounds containing acetoacetate groups, especially acetoacetylated polyols, butyrolactone, carbonates, aldehydes, and also isocyanates, and silicones containing reactive groups;

polymers, especially polyamides, polysulfides, polyvinylformal (PVF), polyvinylbutyral (PVB), polyurethanes (PUR), polymers with carboxyl groups, polyamides, butadiene-acrylonitrile copolymers, styrene-acrylonitrile copolymers, butadiene-styrene copolymers, homo- or copolymers of unsaturated monomers, particularly from the group encompassing ethylene, propylene, butylene, isobutylene, isoprene, vinyl acetate, and alkyl (meth)acrylates, more particularly chlorosulfonated polyethylenes and fluorine-containing polymers, sulfonamide-modified melamines, and purified montan waxes;

inorganic and organic fillers, as for example ground or precipitated calcium carbonates, optionally coated with fatty acids, especially with stearates, or barite (heavy spar), talcs, finely ground quartzes, silica sand, micaceous iron ore, dolomites, wollastonites, kaolins, mica (potassium aluminum silicate), molecular sieves, aluminum oxides, aluminum hydroxides, magnesium hydroxide, silicas, cements, gypsums, flyashes, carbon black, graphite, metal powders such as aluminum, copper, iron, zinc, silver or steel, PVC powders or hollow beads;

fibers, especially glass fibers, carbon fibers, metal fibers, ceramic fibers or polymeric fibers such as polyamide fibers or polyethylene fibers;

pigments, especially titanium dioxide and/or iron oxides;

the aforementioned accelerators;

rheological modifiers, especially thickeners or antisettling agents;

adhesion promoters, especially organoalkoxysilanes;

stabilizers to counter oxidation, heat, light, and UV radiation;

flame retardants, especially aluminum hydroxide (ATH), magnesium dihydroxide (MDH), antimony trioxide, antimony pentoxide, boric acid ($B(OH)_3$), zinc borate, zinc phosphate, melamine borate, melamine cyanurate, ammonium polyphosphate, melamine phosphate, melamine pyrophosphate, polybrominated diphenyl oxides or diphenyl ethers, phosphates such as, in particular, diphenyl cresyl phosphate, resorcinol bis(diphenyl phosphate), resorcinol diphosphate oligomer, tetra-phenylresorcinol diphosphite, ethylenediamine diphosphate or bisphenol A bis(diphenyl phosphate), tris(chloroethyl) phosphate, tris(chloropropyl) phosphate and tris(dichloroisopropyl) phosphate, tris[3-bromo-2,2-bis(bromomethyl)propyl]phosphate, tetrabromobisphenol A, bis(2,3-dibromopropyl ether) of bisphenol A, brominated epoxy resins, ethylene-bis(tetrabromophthalimide), ethylenebis(dibromonorbornanedicarboximide), 1,2-bis(tribromophenoxy)ethane, tris(2,3-dibromopropyl)isocyanurate, tribromophenol, hexabromocyclododecane, bis(hexachlorocyclopentadieno)cyclooctane or chlorinated paraffins;

surface-active substances, especially wetting agents, flow control agents, deaerating agents and/or defoamers;

biocides, such as algicides, fungicides, or substances which inhibit fungal growth, for example.

The epoxy resin composition preferably comprises further auxiliaries and additives, especially wetting agents, flow control agents, defoamers, stabilizers, pigments and/or accelerators, more particularly salicylic acid and/or 2,4,6-tris(dimethylaminomethyl)phenol.

The epoxy resin composition preferably contains no unincorporable diluents or only a low level thereof, more preferably less than 10 weight %, more particularly less than 5 weight %, most preferably less than 2 weight %.

In the epoxy resin composition, the ratio of the number of groups that are reactive toward epoxide groups to the number of epoxide groups is preferably in the range from 0.5 to 1.5, more particularly 0.7 to 1.2.

The amine hydrogens present in the epoxy resin composition, and any further groups present that are reactive toward epoxide groups, react with the epoxide groups in a reaction which entails their ring opening (addition reaction). As a result of these reactions, the composition polymerizes and ultimately cures.

The person skilled in the art is aware that primary amino groups are difunctional with respect to epoxide groups, and that one primary amino group therefore counts as two groups reactive toward epoxide groups.

In particular the epoxy resin composition is a two-pack composition consisting of
(i) a resin component comprising at least one epoxy resin, and
(ii) a hardener component comprising the hardener described.

The components of the two-pack composition are each stored in a dedicated container. Further constituents of the two-pack epoxy resin composition may be present as part of the resin component or of the hardener component; further constituents that are reactive toward epoxide groups are preferably part of the hardener component. A suitable container for storing the resin component or the hardener component is, in particular, a drum, a hopper, a pouch, a pail, a canister, a cartridge or a tube. The components are storable, meaning that they can be kept for several months up to a year or more before being employed, without suffering alteration in their respective properties to any extent relevant for their use. For the use of the two-pack epoxy resin composition, the resin component and the hardener component are mixed with one another shortly before or during application. The mixing ratio between the two components is preferably selected such that the groups of the hardener component that are reactive toward epoxy groups are present in an appropriate ratio relative to the epoxide groups of the resin component, as described above. In terms of parts by weight, the mixing ratio between the resin component and the hardener component is customarily in the range from 1:10 to 10:1.

The two components are mixed by means of a suitable method; this may take place continuously or batchwise. If mixing takes place prior to application, it should be ensured that not too much time elapses between the mixing of the components and application, since otherwise there may be disruptions, such as a retarded or incomplete development of adhesion to the substrate, for example. Mixing takes place in particular at ambient temperature, which is typically in the range from about 5 to 50° C., preferably at about 10 to 30° C.

The mixing of the two components is at the same time the start of curing through chemical reaction, as described above. Curing takes place in particular at ambient temperature. It typically extends over several days to weeks, until it is largely concluded under the prevailing conditions. The duration is dependent on factors including the temperature, the reactivity of the constituents and their stoichiometry, and also the presence of accelerators.

The invention accordingly further provides a cured composition obtained from the curing of an epoxy resin composition as described in the present document.

The epoxy resin composition is applied to at least one substrate, those below being particularly suitable:
glass, glass-ceramic, concrete, mortar, brick, tile, plaster, and natural stone such as granite or marble;
metals and alloys, such as aluminum, iron, steel, or nonferrous metals, including surface-enhanced metals or alloys, such as galvanized or chromed metals;
leather, textiles, paper, wood, woodbase materials bonded with resins, such as with phenolic, melamine or epoxy resins, resin-textile composites, or other polymer composites;
plastics, especially rigid and flexible PVC, ABS, polycarbonate (PC), polyamide (PA), polyesters, PMMA, epoxy resins, PUR, POM, PO, PE, PP, EPM or EPDM, the plastics having optionally been surface-treated by plasma, corona or flame treatment;
fiber-reinforced plastics, such as carbon fiber-reinforced plastics (CRP), glass fiber-reinforced plastics (GRP) or sheet molding compounds (SMC);
coated substrates, such as powder-coated metals or alloys;
paints or varnishes.

As and when necessary, the substrates may be pretreated before the epoxy resin composition is applied. Such pretreatments include, in particular, physical and/or chemical cleaning techniques, as for example sanding, sand blasting, shot blasting, brushing and/or blowing, and also, furthermore, treatment with cleaners or solvents, or the application of an adhesion promoter, an adhesion promoter solution or a primer.

The epoxy resin composition described can be used with advantage as a constituent of fiber composite materials, as an encapsulating compound, sealant, adhesive, covering, coating, paint, varnish, seal, priming coat or primer.

In particular it may be used as encapsulant, sealant, and adhesive, such as an electrical encapsulant, sealing compound, vehicle body adhesive, sandwich element adhesive, half-shell adhesive, for rotor blades of wind turbines, for example, bridge element adhesive or anchoring adhesive; and also, moreover, as covering, coating, paint, varnish, seal, priming coat, and primer for construction and industrial applications, such as in particular, as floorcovering and floor coating for interiors such as offices, industrial halls, sports halls or cooling chambers, or outdoors for balconies, terraces, parking decks, bridges or roofs, as protective coating for concrete, cement, metals, plastics or wood, as for example to seal the surfaces of wooden constructions, vehicles, loading areas, tanks, silos, shafts, piping circuits, pipelines, machines or steel constructions, such as of boats, piers, offshore platforms, sluice gates, hydroelectric power stations, river constructions, swimming pools, wind turbines, bridges, chimneys, cranes or sheet-pile walls; and also, furthermore, as undercoat, tie coat, anticorrosion primer, or for rendering surfaces water-repellent. The fully or partly cured epoxy resin composition, especially when used as a coating, covering or paint, may have a further coating, a further covering or a further paint applied to it, in which case this further layer may likewise be an epoxy resin composition, or else a different material, more particularly a polyurethane coating or polyurea coating.

The epoxy resin composition described can be used with particular advantage as a coating. Coating in this context includes two-dimensionally applied coverings of all kinds, including in particular paints, varnishes, seals, priming coats, and primers, as described above. With more particular advantage the epoxy resin composition described can be used in low-emission products that carry eco-quality seals, according for example to Emicode (EC1 Plus), AgBB, DIBt, Der Blaue Engel, AFSSET, RTS (M1), and US Green Building Council (LEED).

As a coating, the epoxy resin composition is used advantageously in a method for coating, where it has a liquid consistency with low viscosity and good leveling properties and can be applied in particular as a self-leveling coating to predominantly planar surfaces or as a paint. The epoxy resin composition in this application, immediately after the mixing of the resin and hardener components, preferably has a viscosity as measured at 20° C. in the range from 300 to 3000 mPa·s, preferably in the range from 300 to 2000 mPa·s, more preferably in the range from 300 to 1500 mPa·s. Within the working time, the mixed composition is applied two-dimensionally as a thin film with a film thickness of typically about 50 μm to about 5 mm to a substrate, typically at ambient temperature. Application takes place in particular by pouring the composition onto the substrate that is to be coated, and then distributing it evenly with the aid, for example, of a doctor blade or toothed applicator. Application may alternatively take place with a brush or roller or by spray application, as an anticorrosion coating on steel, for example.

Curing is typically accompanied by the development of largely clear, glossy, and nonsticky films of high hardness, which exhibit effective adhesion to a very wide variety of substrates.

The invention further provides an article comprising a cured composition obtained by curing the epoxy resin composition described. This cured composition is more particularly in the form of a coating.

The epoxy resin composition described is notable for advantageous properties. It is of very low viscosity and odor and cures rapidly, even under damp and cold conditions, and largely without blushing effects, even when the fractions of unincorporable diluents are small or none are used at all, and in particular also without the use of volatile, intensely odorous amines. In two-dimensional use, clear, nonsticky films are produced which have high hardness and high surface quality, and which suffer virtually no yellowing under the effect of light. With the epoxy resin composition described, it is possible in particular to have access to low-emission epoxy resin products which meet the conditions for many eco-quality seals and at the same time satisfy exacting requirements in terms of operational safety, processing properties, and service properties.

EXAMPLES

Set out below are working examples which are intended to elucidate in more detail the invention described. The invention is of course not confined to these working examples that are described.

"AHEW" stands for the amine hydrogen equivalent weight.

"EEW" stands for the epoxide equivalent weight.

1. Description of Measurement Methods

Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers (cm$^{-1}$) (measuring window: 4000-650 cm$^{-1}$).

The viscosity was measured on a thermostated cone/plate viscometer, Rheotec RC30 (cone diameter 50 mm, cone angle 1°, cone tip/plate distance 0.05 mm, shear rate 10 s$^{-1}$).

The amine number was determined by titration (with 0.1N HClO$_4$ in acetic acid against crystal violet).

The melting point was determined by means of DMTA measurement in the temperature range from −50° C. to 25° C., at 5 K/min and 10 Hz.

2. Commercial Substances Used

Araldite® DY-K: (from Huntsman), 2-cresyl glycidyl ether, EEW about 183 g/eq
Araldite® DY-P: (from Huntsman), p-tert-butylphenyl glycidyl ether, EEW about 225 g/eq
Cardolite® LITE (from Cardolite), glycidyl ether of cardanol, EEW about 2513HP: 415 g/eq
Araldite® GY 250: (from Huntsman), bisphenol A diglycidyl ether, EEW about 187.5 g/eq
Araldite® DY-E: (from Huntsman), monoglycidyl ether of C$_{12}$ to C$_{14}$ alcohols, EEW about 290 g/eq
Ancamine® K 54: (from Air Products), 2,4,6-tris(dimethylaminomethyl)phenol
Dytek® A: (from Invista), 1,5-diamino-2-nnethylpentane, AHEW
MXDA: (from Mitsubishi Gas Chemical), 1,3-bis(aminomethyl)-benzene
Gaskamine® 240: (from Mitsubishi Gas Chemical), styrenized 1,3-bis(aminomethyl)benzene, AHEW about 103 g/eq
Jeffamine® D-230: (from Huntsman), polyoxypropylenediamine with average molecular weight of about 240 g/mol, AHEW 60 g/eq
Jeffamine® RFD-270: (from Huntsman), cycloaliphatic diamine containing ether groups, from the propoxylation and subsequent amination of 1,4-dimethylolcyclohexane, average molecular weight about 270 g/mol, AHEW 67 g/eq
Vestamin® TMD: (from Evonik), 2,2,4- and 2,4,4-trimethylhexamethylenediamine, AHEW 39.6 g/eq
1,3-BAC: (from Mitsubishi Gas Chemical), 1,3-bis(aminomethyl)cyclohexane, AHEW 35.5 g/eq

3. Preparation of Amines

Amine A-1: 1-((2-Aminopropyl)amino)-3-(2-methylphenoxy)propan-2-ol 4.15 kg (56 mol) of 1,2-propylenediamine were introduced under a nitrogen atmosphere and heated to 70° C., and slowly 2.93 kg (16 mol) of Araldite® DY-K were added, accompanied by thorough stirring, the temperature of the reaction mixture being held by cooling at between 70 and 80° C. The reaction mixture was left at 80° C. for an hour, then cooled and freed of its volatile constituents on a thin-film evaporator (0.5-1 mbar, jacket temperature 115° C.). This gave a clear, slightly yellowish liquid having a viscosity at 20° C. of 3.3 Pa·s, an amine number of 478.7 mg KOH/g, a purity of 91.5% (determined by gas chromatography, 8.5% 1,3-bis(2-methylphenoxy)propan-2-ol from Araldite® DY-K), a melting point of −25° C., and a theoretical AHEW of about 85.7 g/eq. FT-IR: 3025, 2955, 2918, 1601, 1590, 1494, 1456, 1377, 1307, 1288, 1242, 1191, 1120, 1050, 1035, 926, 837, 748, 713.

Amine A-2: 1-((2-Aminopropyl)amino)-3-(4-tert-butylphenoxy)propan-2-ol 77.4 g (1.04 mol) of 1,2-propylenediamine were introduced under a nitrogen atmosphere and heated to 70° C., and slowly 67.5 g (0.3 mol) of Araldite® DY-P were added, accompanied by thorough stirring. The reaction mixture was left at 80° C. for 2 hours. The volatile constituents were then removed on a rotary evaporator at 65° C. and 1 mbar over 3 hours. This gave a clear, slightly yellowish liquid having a viscosity of 105 Pa·s, an amine number of 374.9 mg KOH/g, and a theoretical AHEW of about 99.7 g/eq.

Amine A-3

As described for amine A-2, 51.9 g (0.7 mol) of 1,2-propylenediamine were reacted with 83.0 g (0.2 mol) of Cardolite® LITE 2513HP. This gave a clear, slightly yellowish liquid having a viscosity of 1.93 Pas, an amine number of 204.3 mg KOH/g, and a theoretical AHEW of about 163.0 g/eq.

Amine A-4: (Comparative)

As described for amine A-1, 4.65 kg (40 mol) of Dytek® A were reacted with 1.83 kg (10 mol) of Araldite® DY-K, the jacket temperature of the thin-film evaporator being 160° C. This gave a clear, slightly yellowish liquid having a viscosity at 20° C. of 6.5 Pa's, an amine number of 367.1 mg KOH/g, and a theoretical AHEW of about 99.7 g/eq.

Amine A-5: (Comparative)

As described for amine A-2, 96.2 g (1.6 mol) of ethylenediamine were reacted with 73.2 g (0.4 mol) of Araldite® DY-K. This gave a clear, slightly yellowish liquid having a viscosity of 8.26 Pas, an amine number of 484.9 mg KOH/g, and a theoretical AHEW of about 81.0 g/eq.

Amines A-1 to A-3 are amines of the formula (I); the amines A-4 and A-5 serve for comparison.

4. Preparation of Alkylated Amines

Benzylated MXDA

In a round-bottomed flask, 17.0 g (0.16 mol) of benzaldehyde and 13.6 g (0.10 mol) of MXDA were dissolved under a nitrogen atmosphere in a sufficient quantity of isopropanol. The solution was stirred at 23° C. for 30 minutes and then subjected to hydrogenation under a hydrogen pressure of 80 bar at a temperature of 80° C. with a flow rate of 3 ml/min on a continuously operating hydrogenation apparatus with Pd/C fixed bed catalyst. For reaction monitoring, IR spectroscopy was used to verify whether the imine band at about 1665 $cm^{-1}$ had disappeared. Thereupon, the solution was concentrated under reduced pressure at 80° C. This gave a clear, yellowish oil having a viscosity of 0.1 Pas at 20° C., an amine number of 416.8 mg KOH/g, and a theoretical AHEW of about 115.5 g/eq.

Ethylhexylated MXDA

In the same way as described for the benzylated MXDA, 25.6 g (0.20 mol) of 2-ethylhexanal and 13.6 g (0.10 mol) of MXDA were reacted. This gave a clear, slightly yellowish liquid having a viscosity of 140 mPa·s at 20° C., an amine number of 308.6 mg KOH/g, and a theoretical AHEW of about 180.3 g/eq.

5. Production of Hardeners and Epoxy Resin Compositions

For each example, the ingredients specified in Tables 1 to 4 were mixed in the specified amounts (in parts by weight) of the hardener component by means of a centrifugal mixer (SpeedMixer™ DAC 150, FlackTek Inc.) and stored in the absence of moisture.

Similarly, the ingredients of the resin component as specified in Tables 1 to 4 were processed and stored.

Subsequently the two components of each composition were processed to a homogeneous liquid using the centrifugal mixer, and this liquid was immediately tested as follows: 10 minutes after mixing, the viscosity at 20° C. was ascertained ("viscosity (10')").

A first film was drawn down in a thickness of 500 µm onto a glass plate, which was stored at 23±1° C. and 50±5% relative humidity (i.e., standard conditions, abbreviated below to "SC"), and cured. The KÖnig hardness (pendulum hardness by König method, measured according to DIN EN ISO 1522) of this film was ascertained after 2 days ("König hardness (SC) (2d)"), after 4 days ("König hardness (SC) (4d)"), after 7 days ("König hardness (SC) (7d)"), and after 14 days ("König hardness (SC) (14 d)"). After 14 days, the aspect of the film was assessed (designated in the table as "aspect (SC)"). A film designated "attractive" was clear and had a glossy and nonsticky surface without structure. "Structure" in this context is any kind of marking or pattern on the surface.

A second film was drawn down in a thickness of 500 µm onto a glass plate, which, immediately after application, was stored for 7 days at 8° C. and 80% relative humidity and then for 3 weeks under SC, and cured. 24 hours after application, a polypropylene bottle cap was placed on the film, with a moist piece of sponge placed beneath it. After a further 24 hours, the sponge and the cap were removed, and were placed at a new site on the film, then removed again after 24 hours and placed at a new site, a total of 4 times. Subsequently the aspect of this film was assessed (identified in the tables as "aspect (8°/80%)"), in the same way as described for the aspect (SC). In this case each time the number of markings was also indicated that were visible in the film as a result of the moist sponge and/or the applied cap. Once again, the König hardness of the films cured in this way was ascertained, in each case after 7 days at 8° C. and 80% relative humidity ("König h. (7 d 8°/80%)"), then after a further 2 days under SC ("König h. (+2 d SC)"), 7 days under SC ("König h. (+7 d SC)"), and after 14 days under SC ("König h. (+14 d SC)").

The results are recorded in Tables 1 to 4.

The epoxy resin compositions EZ-1 to EZ-16 are inventive examples. The epoxy resin compositions Ref-1 to Ref-9 are comparative examples.

TABLE 1

Composition and properties of EZ-1 to EZ-4 and Ref-1 to Ref-3.

| Example | EZ-1 | EZ-2 | EZ-3 | EZ-4 | Ref-1 | Ref-2 | Ref-3 |
|---|---|---|---|---|---|---|---|
| Resin comp.: | | | | | | | |
| Araldite ® GY-250 | 167.2 | 167.2 | 167.2 | 167.2 | 167.2 | 167.2 | 167.2 |
| Araldite ® DY-E | 31.8 | 31.8 | 31.8 | 31.8 | 31.8 | 31.8 | 31.8 |
| Hardener comp.: | | | | | | | |
| Amine | A-1 | A-1 | A-2 | A-3 | A-4 | A-4 | A-5 |
|  | 85.7 | 85.7 | 99.7 | 163.0 | 99.7 | 99.7 | 81.0 |
| Ancamine ® K 54 | — | 2.8 | 2.9 | 2.9 | — | 2.9 | 2.8 |
| Viscosity (10') [Pa · s] | 2.19 | 2.24 | 6.05 | 1.81 | 3.49 | 3.63 | 8.51 |
| König       (1 d SC) | 105 | 137 | 119 | n.m. | 64 | 101 | 151 |
| hardness   (2 d SC) | 165 | 186 | 175 | 9 | 98 | 139 | 176 |
| [s]           (4 d SC) | 199 | 210 | 204 | 18 | 125 | 166 | 195 |

TABLE 1-continued

Composition and properties of EZ-1 to EZ-4 and Ref-1 to Ref-3.

| Example | | EZ-1 | EZ-2 | EZ-3 | EZ-4 | Ref-1 | Ref-2 | Ref-3 |
|---|---|---|---|---|---|---|---|---|
| | (7 d SC) | 214 | 221 | 220 | 27 | 148 | 182 | 200 |
| | (14 d SC) | 218 | 220 | 221 | 38 | 171 | 180 | 204 |
| Aspect (SC) | | attractive | attractive | attractive | attractive | attractive | attractive | milky |
| König h. [s] | (7 d 8°/80%) | 59 | 81 | 83 | n.m. | 35 | 52 | 87 |
| | (+2 d SC) | 175 | 183 | 181 | n.m. | 88 | 126 | 172 |
| | (+7 d SC) | 206 | 198 | 221 | n.m. | 125 | 168 | 196 |
| | (+14 d SC) | 205 | 203 | 220 | n.m. | 151 | 175 | 198 |
| Aspect (8°/80%) | | attractive | attractive | attractive | sticky | attractive | attractive | milky |
| Number of marks | | 1 | 1 | 2 | n.d. | 1 | 1 | 3 |

"n.m." stands for "not measurable".
"n.d." stands for "not determined".

TABLE 2

Composition and properties of EZ-5 to EZ-11.

| Example | | EZ-5 | EZ-6 | EZ-7 | EZ-8 | EZ-9 | EZ-10 | EZ-11 |
|---|---|---|---|---|---|---|---|---|
| Resin comp.: | | | | | | | | |
| Araldite ® GY-250 | | 167.2 | 167.2 | 167.2 | 167.2 | 167.2 | 167.2 | 167.2 |
| Araldite ® DY-E | | 31.8 | 31.8 | 31.8 | 31.8 | 31.8 | 31.8 | 31.8 |
| Hardener comp.: | | | | | | | | |
| Amine | | A-1 | A-1 | A-1 | A-1 | A-1 | A-1 | A-2 |
| | | 51.4 | 34.3 | 42.9 | 42.9 | 42.9 | 42.9 | 59.8 |
| Jeffamine ® D-230 | | 24.0 | 24.0 | — | 18.0 | 21.0 | 21.0 | 24.0 |
| Jeffamine ® RFD-270 | | — | — | 20.1 | — | — | — | — |
| Gaskamine ® 240 | | — | 20.6 | — | — | — | — | — |
| Ethylhexylated MXDA | | — | — | 36.0 | — | — | — | — |
| Benzylated MXDA | | — | — | — | 23.1 | — | — | — |
| 1,3-BAC | | — | — | — | — | 5.3 | — | — |
| Vestamin ®TMD | | — | — | — | — | — | 5.9 | — |
| Ancamine ® K 54 | | 2.7 | 2.8 | 3.0 | 2.8 | 2.7 | 2.7 | 2.8 |
| Viscosity (10') [Pa · s] | | 1.07 | 0.79 | 0.56 | 0.91 | 0.97 | 0.94 | 1.73 |
| König hardness [s] | (1 d SC) | 74 | 75 | 33 | 74 | 84 | 46 | 60 |
| | (2 d SC) | 160 | 148 | 81 | 153 | 122 | 104 | 143 |
| | (4 d SC) | 185 | 186 | 110 | 190 | 170 | 181 | 198 |
| | (7 d SC) | 206 | 200 | 133 | 203 | 171 | 206 | 219 |
| | (14 d SC) | 207 | 218 | 143 | 213 | 179 | 214 | 218 |
| Aspect (SC) | | attractive | attractive | attractive | attractive | sl. structure | attractive | attractive |
| König h. [s] | (7 d 8°/80%) | 50 | 47 | 25 | 47 | 33 | 24 | 53 |
| | (+2 d SC) | 151 | 160 | 77 | 167 | 104 | 81 | 165 |
| | (+7 d SC) | 165 | 206 | 111 | 203 | 151 | 116 | 193 |
| | (+14 d SC) | 168 | 205 | 115 | 204 | 153 | 121 | 198 |
| Aspect (8°/80%) | | attractive | attractive | attractive | attractive | attractive | attractive | attractive |
| Number of marks | | 1 | 1 | none | 1 | 2 | 2 | 2 |

"sl." stands for "slight"

TABLE 3

Composition and properties of Ref-4 to Ref-9.

| Example | Ref-4 | Ref-5 | Ref-6 | Ref-7 | Ref-8 | Ref-9 |
|---|---|---|---|---|---|---|
| Resin comp.: | | | | | | |
| Araldite ® GY-250 | 167.2 | 167.2 | 167.2 | 167.2 | 167.2 | 167.2 |
| Araldite ® DY-E | 31.8 | 31.8 | 31.8 | 31.8 | 31.8 | 31.8 |
| Hardener comp.: | | | | | | |
| Amine | A-4 | A-4 | A-4 | A-5 | A-5 | A-5 |
| | 59.8 | 39.9 | 49.9 | 48.6 | 32.4 | 40.5 |
| Jeffamine ® D-230 | 24.0 | 24.0 | 21.0 | 24.0 | 24.0 | 21.0 |
| Gaskamine ® 240 | — | 20.6 | — | — | 20.6 | — |

TABLE 3-continued

Composition and properties of Ref-4 to Ref-9.

| Example | | Ref-4 | Ref-5 | Ref-6 | Ref-7 | Ref-8 | Ref-9 |
|---|---|---|---|---|---|---|---|
| 1,3-BAC | | — | — | 5.3 | — | — | 5.3 |
| Ancamine ® K 54 | | 2.8 | 2.8 | 2.7 | 2.7 | 2.8 | 2.7 |
| Viscosity (10") [Pa · s] | | 1.21 | 0.93 | 1.13 | 2.13 | 0.97 | 1.24 |
| König hardness [s] | (1 d SC) | 50 | 42 | 75 | 89 | 63 | 108 |
| | (2 d SC) | 112 | 102 | 148 | 141 | 123 | 158 |
| | (4 d SC) | 155 | 155 | 186 | 181 | 166 | 190 |
| | (7 d SC) | 183 | 173 | 195 | 191 | 183 | 202 |
| | (14 d SC) | 200 | 192 | 203 | 204 | 197 | 213 |
| Aspect (SC) | | attractive | attractive | attractive | sl. milky | attractive | attractive |
| König h. [s] | (7 d 8°/80%) | 35 | 25 | 26 | 47 | 32 | 29 |
| | (+2 d SC) | 132 | 111 | 46 | 151 | 109 | 91 |
| | (+7 d SC) | 175 | 169 | 77 | 182 | 160 | 119 |
| | (+14 d SC) | 188 | 176 | 79 | 185 | 164 | 122 |
| Aspect (8°/80%) Number of marks | | attractive 1 | attractive 1 | sl. sticky 2 | sl. milky 1 | attractive 1 | attractive 2 |

"sl." stands for "slightly"

TABLE 4

Composition and properties of EZ-12 to EZ-16.

| | | Example | | | | |
|---|---|---|---|---|---|---|
| | | EZ-12 | EZ-13 | EZ-14 | EZ-15 | EZ-16 |
| Resin comp.: | | | | | | |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Hardener comp.: | | | | | | |
| Amine | | A-1 | A-1 | A-1 | A-1 | A-1 |
| | | 79.5 | 89.9 | 47.7 | 54.0 | 31.8 |
| Jeffamine ® D-230 | | — | — | 24.0 | 24.0 | 24.0 |
| Gaskamine ® 240 | | — | — | — | — | 20.6 |
| Salicylic acid[1] | | 1.6 | 4.8 | 1.0 | 2.9 | 1.6 |
| Ancamine ® K 54 | | 0.8 | 1.9 | 0.7 | 1.2 | 0.8 |
| Viscosity (10') [Pa · s] | | 2.86 | 11.10 | 1.16 | 2.40 | 0.92 |
| König hardness [s] | (1 d SC) | 115 | 83 | 56 | 45 | 43 |
| | (2 d SC) | 171 | 150 | 146 | 126 | 111 |
| | (4 d SC) | 200 | 185 | 188 | 178 | 169 |
| | (7 d SC) | 219 | 197 | 209 | 197 | 189 |
| | (14 d SC) | 219 | 217 | 211 | 213 | 201 |
| Aspect (SC) | | attractive | attractive | attractive | attractive | attractive |
| König h. [s] | (7 d 8°/80%) | 68 | 59 | 42 | 36 | 36 |
| | (+2 d SC) | 175 | 171 | 161 | 148 | 148 |
| | (+7 d SC) | 219 | 199 | 185 | 192 | 175 |
| | (+14 d SC) | 216 | 218 | 203 | 207 | 188 |
| Aspect (8°/80%) Number of marks | | attractive 1 | attractive 1 | attractive 1 | attractive none | attractive 1 |

[1]dissolved in the premixed amines

The invention claimed is:

1. An amine of the formula (I),

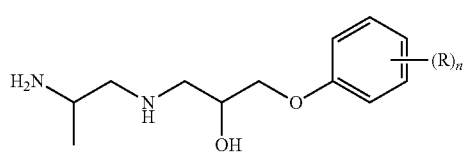

(I)

where
R is an alkyl, cycloalkyl, aralkyl or alkoxy radical having 1 to 22 carbon atoms which optionally comprises unsaturated fractions; and
n is 0 or 1 or 2 or 3.

2. The amine as claimed in claim 1, wherein n is 1.

3. The amine as claimed in claim 1, wherein R is methyl.

4. A process for preparing an amine as claimed in claim 1 comprising reacting 1,2-propylenediamine with an aryl glycidyl ether in a 1,2-propylenediamine/aryl glycidyl ether molar ratio in a range from 1.1 to 5, and subsequent distillative removal of unreacted 1,2-propylenediamine.

5. A method of hardening epoxy resins by mixing a hardener comprising the amine of formula (I) as claimed in claim 1 with at least one epoxy resin.

6. The method as claimed in claim 5, wherein the hardener comprises the amine of formula (I) in an amount such that 5 to 100% of the amine hydrogens in the hardener that are reactive toward epoxide groups originate from the amine of the formula (I).

7. The method as claimed in claim 5, wherein the hardener comprises at least one further polyamine having at least two amine hydrogens that are active toward epoxide groups.

8. The method as claimed in claim 7, wherein the further polyamine is a primary diamine selected from the group consisting of 2,2,4- and 2,4,4-trimethylhexamethylenediamine, 1-amino-3-aminomethyl-3,5,5-trimethylcyclohexane, 1,3-bis(aminomethyl)benzene, 1,3-bis(aminomethyl)cyclohexane, 1,4-bis(aminomethyl)cyclohexane, bis(4-aminocyclohexyl)methane, bis(4-amino-3-methylcyclohexyl)methane, 2,5(2,6)-bis(aminomethyl)bicyclo[2.2.1]heptane, 3(4),8(9)-bis(aminomethyl)tricyclo[5.2.1.0$^{2,6}$]decane, and polyamines containing ether groups and having an average molecular weight of up to 500 g/mol.

9. The method as claimed in claim 7, wherein the further polyamine is a polyamine having at least one secondary amino group, selected from the group consisting of N-monoalkylated 1,6-hexanediamine, N,N'-dialkylated 1,6-hexanediamine, N-monoalkylated 1,5-diamino-2-methylpentane, N,N'-dialkylated 1,5-diamino-2-methylpentane, N-monoalkylated 1,3-bis(aminomethyl)cyclohexane, N,N'-dialkylated 1,3-bis(aminomethyl)cyclohexane, N-monoalkylated 1,4-bis(aminomethyl)cyclohexane, N,N'-dialkylated 1,4-bis(aminomethyl)cyclohexane, N-monoalkylated 1,3-bis(aminomethyl)benzene, N,N'-dialkylated 1,3-bis(aminomethyl)benzene, N-monoalkylated bis(hexamethylene)triamine, N,N'-dialkylated bis(hexamethylene)triamine, N-monoalkylated diethylenetriamine, N,N'-dialkylated diethylenetriamine, N-monoalkylated triethylenetetramine, N,N'-dialkylated triethylenetetramine, N monoalkylated tetraethylenepentamine, N,N'-dialkylated tetraethylenepentamine, N-monoalkylated dipropylenetriamine, N,N'-dialkylated dipropylenetriamine, N-monoalkylated N-(2-aminoethyl)-1,3-propanediamine, N,N'-dialkylated N-(2-aminoethyl)-1,3-propanediamine, N-monoalkylated N,N'-bis(aminopropyl)-1,4-diaminobutane and N,N'-dialkylated N,N'-bis(aminopropyl)-1,4-diaminobutane, the alkyl groups being selected in each case from the group consisting of benzyl, 2-phenylethyl, isobutyl, hexyl, and 2-ethylhexyl.

10. The method as claimed in claim 7, wherein the further polyamine is a diamine containing ether groups.

11. The method as claimed in claim 5, wherein the hardener contains less than 25 weight % of unincorporable diluents.

12. An epoxy resin composition comprising at least one epoxy resin and a hardener as described in claim 5.

13. The epoxy resin composition as claimed in claim 12, wherein it is a two-pack composition consisting of
(i) a resin component comprising at least one epoxy resin, and
(ii) a hardener component comprising the hardener.

14. A cured composition obtained from the curing of an epoxy resin composition as claimed in claim 12.

15. An article comprising a cured composition as claimed in claim 14.

16. The amine as claimed in claim 1, wherein R is methyl or tert-butyl.

* * * * *